United States Patent
Takeno et al.

(10) Patent No.: US 11,633,096 B2
(45) Date of Patent: Apr. 25, 2023

(54) OPHTHALMOLOGIC IMAGE PROCESSING DEVICE AND NON-TRANSITORY COMPUTER-READABLE STORAGE MEDIUM STORING COMPUTER-READABLE INSTRUCTIONS

(71) Applicant: NIDEK CO., LTD., Gamagori (JP)

(72) Inventors: Naoki Takeno, Gamagori (JP); Ryosuke Shiba, Gamagori (JP); Sohei Miyazaki, Gamagori (JP); Yusuke Sakashita, Okazaki (JP); Yoshiki Kumagai, Toyokawa (JP)

(73) Assignee: NIDEK CO., LTD., Gamagori (JP)

( * ) Notice: Subject to any disclaimer, the term of this patent is extended or adjusted under 35 U.S.C. 154(b) by 475 days.

(21) Appl. No.: 16/778,257

(22) Filed: Jan. 31, 2020

(65) Prior Publication Data
US 2020/0245858 A1  Aug. 6, 2020

(30) Foreign Application Priority Data

Jan. 31, 2019 (JP) ............................. JP2019-016062
Jan. 31, 2019 (JP) ............................. JP2019-016063

(51) Int. Cl.
*G06V 10/00* (2022.01)
*A61B 3/00* (2006.01)
(Continued)

(52) U.S. Cl.
CPC .......... *A61B 3/0025* (2013.01); *A61B 3/0041* (2013.01); *A61B 3/102* (2013.01);
(Continued)

(58) Field of Classification Search
CPC ..... A61B 3/0025; A61B 3/102; A61B 3/0041; A61B 5/7267; A61B 3/12;
(Continued)

(56) References Cited

U.S. PATENT DOCUMENTS

2011/0190657 A1* 8/2011 Zhou ...................... G16H 50/70
600/558
2012/0050308 A1* 3/2012 Nakano ...................... G06T 5/50
345/592

(Continued)

FOREIGN PATENT DOCUMENTS

JP  2018-046958 A  3/2018
JP  2018-051223 A  4/2018
(Continued)

OTHER PUBLICATIONS

Jun. 24, 2020 Extended European Search Report issued in International Patent Application No. 20154533.2.
(Continued)

Primary Examiner — Li Liu
(74) Attorney, Agent, or Firm — Oliff PLC

(57) ABSTRACT

A processor of an ophthalmologic image processing device acquires an ophthalmologic image photographed by an ophthalmologic image photographing device. The processor inputs the ophthalmologic image into a mathematical model trained by a machine learning algorithm to acquire a result of an analysis relating to at least one of a specific disease and a specific structure of a subject eye. The processor acquires information of a distribution of weight relating to an analysis by a mathematical model, as supplemental distribution information, for which an image area of the ophthalmologic image input into the mathematical model is set as a variable. The processor sets a part of the image area of the ophthalmologic image, as an attention area, based on the supplemental distribution information. The processor acquires an image of a tissue including the attention area among a tissue of the subject eye and displays the image on a display unit.

11 Claims, 12 Drawing Sheets

(51) Int. Cl.
    *G16H 30/40*     (2018.01)
    *G06N 20/00*     (2019.01)
    *A61B 3/10*     (2006.01)
    *G06V 10/25*     (2022.01)

(52) U.S. Cl.
    CPC ............. *G06N 20/00* (2019.01); *G06V 10/25* (2022.01); *G16H 30/40* (2018.01)

(58) Field of Classification Search
    CPC . G06T 2207/30041; G06T 2207/10101; G06T 2207/20081; G06T 2207/20084
    See application file for complete search history.

(56) References Cited

U.S. PATENT DOCUMENTS

| | | |
|---|---|---|
| 2014/0276025 A1 | 9/2014 | Durbin et al. |
| 2018/0144470 A1 | 5/2018 | Govindjee et al. |
| 2021/0407096 A1* | 12/2021 | Zangwill .................. G06T 3/60 |

FOREIGN PATENT DOCUMENTS

| | | |
|---|---|---|
| JP | 2018-121885 A | 8/2018 |
| JP | 2018-121886 A | 8/2018 |
| WO | 2018/035473 A2 | 2/2018 |

OTHER PUBLICATIONS

Lam, Carson, et al. "Retinal Lesion Detection With Deep Learning Using Image Patches". Investigative Ophthalmology & Visual Science., 2018, vol. 59, No. 1, pp. 590-596.

Oct. 4, 2022 Office Action issued in Japanese Patent Application No. 2019-016062.

Oct. 4, 2022 Office Action issued in Japanese Patent Application No. 2019-016063.

* cited by examiner

OPHTHALMOLOGIC IMAGE PROCESSING DEVICE AND NON-TRANSITORY COMPUTER-READABLE STORAGE MEDIUM STORING COMPUTER-READABLE INSTRUCTIONS

CROSS REFERENCE TO RELATED APPLICATION

This application is based upon and claims the benefit of priority of Japanese Patent Application No. 2019-016062 and Japanese Patent Application No. 2019-016063, filed on Jan. 31, 2019, the contents of which are incorporated herein by reference in their entirety.

BACKGROUND

The present disclosure relates to an ophthalmologic image processing device that processes an ophthalmic image of a subject eye and a non-transitory computer-readable storage medium storing computer-readable instructions.

In recent years, a technique that acquires various medical information using a mathematical model trained by a machine learning algorithm has been proposed. For example, an ophthalmologic device disclosed in Japanese Unexamined Patent Application Publication JP 2018-051223 inputs an eye shape parameter into a mathematical model trained by a machine learning algorithm so as to acquire intraocular lens (IOL) related information (for example, a predicted postoperative anterior chamber depth) of a subject eye and calculates a power of an IOL based on the acquired IOL related information.

SUMMARY

It may be considered to input an ophthalmologic image into a mathematical model trained by a machine learning algorithm so as to acquire a result of an analysis relating to at least one of a disease and a structure of a subject eye. However, presence/absence of the disease, a degree of the disease, a structural characteristic or the like in a subject eye is different depending on the subject eye, and therefore variation of certainty might be caused in the result of the analysis. Consequently, it might occur that an operation such as a diagnosis of a user (for example, a doctor or the like) is not appropriately assisted by merely providing the result of the analysis output through the mathematical model to the user.

An object of a first aspect of the present disclosure is to provide an ophthalmologic image processing device and a non-transitory computer-readable storage medium storing computer-readable instructions that can appropriately assist an operation of a user.

Further, it may be possible to acquire results of analyses relating to diseases and structures from one ophthalmologic image. However, in such a case, it might be difficult for a user to recognize a plurality of the results of the analyses efficiently unless a plurality of the results of the analyses is appropriately provided to the user.

An object of a second aspect of the present disclosure is to provide an ophthalmologic image processing device and a non-transitory computer-readable storage medium storing computer-readable instructions that can appropriately provide a result of an analysis relating to a subject eye to a user.

Embodiments of the first aspect provide an ophthalmologic image processing device that processes an ophthalmologic image of a tissue of a subject eye. The processor of the ophthalmologic image processing device: acquires the ophthalmologic image photographed by an ophthalmologic image photographing device; inputs the ophthalmologic image into a mathematical model trained by a machine learning algorithm and acquires a result of an analysis relating to at least one of a specific disease and a specific structure of a subject eye; acquires information of a distribution of weight relating to the analysis by the mathematical model, as supplemental distribution information, for which an image area of the ophthalmologic image input into the mathematical model is set as a variable; sets a part of the image area of the ophthalmologic image, as an attention area, based on the supplemental distribution information; acquires an image of a tissue including the attention area among a tissue of the subject eye; and displays the image on a display unit.

Embodiments of the first aspect provide a non-transitory computer-readable medium storing computer-readable instructions that, when executed by a processor of an ophthalmologic image processing device, causes the ophthalmologic image processing device to perform processes including: acquiring an ophthalmologic image photographed by an ophthalmologic image photographing device; inputting the ophthalmologic image into a mathematical model trained by a machine learning algorithm and acquiring a result of an analysis relating to at least one of a specific disease and a specific structure of a subject eye; acquiring information of a distribution of weight relating to the analysis by the mathematical model, as supplemental distribution information, for which an image area of the ophthalmologic image input into the mathematical model is set as a variable; setting a part of the image area of the ophthalmologic image, as an attention area, based on the supplemental distribution information; acquiring an image of a tissue including the attention area among a tissue of the subject eye; and displaying the image on a display unit.

According to the ophthalmologic image processing device and the non-transitory computer-readable medium storing the computer-readable instructions according to the first aspect of the present disclosure, an operation of a user can be appropriately assisted.

Embodiments of the second aspect provide an ophthalmologic image processing device that processes an ophthalmologic image of a tissue of a subject eye. The processor of the ophthalmologic image processing device: acquires the ophthalmologic image photographed by an ophthalmologic image photographing device; inputs the ophthalmologic image into a mathematical model trained by a machine learning algorithm and acquires results of analyses relating to diseases or structures of a subject eye; acquires a supplemental map, for each of the results of the analyses, that indicates a distribution of weight relating to the analysis by the mathematical model, for which an image area of the ophthalmologic image input into the mathematical model is set as a variable; generates an integration map in which the supplemental maps are integrated within an identical area; and displays the integration map on a display unit.

Embodiments of the second aspect provide a non-transitory computer-readable medium storing computer-readable instructions that, when executed by a processor of an ophthalmologic image processing device, causes the ophthalmologic image processing device to perform processes including: acquiring an ophthalmologic image photographed by an ophthalmologic image photographing device; inputting the ophthalmologic image into a mathematical model trained by a machine learning algorithm and acquiring results of analyses relating to diseases or structures of a subject eye; acquiring a supplemental map, for each of the results of the analyses, that indicates a distribution of weight relating to the analysis by the mathematical model, for which an image area of the ophthalmologic image input into the mathematical model is set as a variable; generating an integration map in which the supplemental maps are integrated within an identical area; and displaying the integration map on a display unit.

According to the ophthalmologic image processing device and the non-transitory computer-readable medium storing the computer-readable instructions according to the second aspect of the present disclosure, the result of the analysis relating to a subject eye can be appropriately provided to a user.

DETAILED DESCRIPTION

Figure 1:
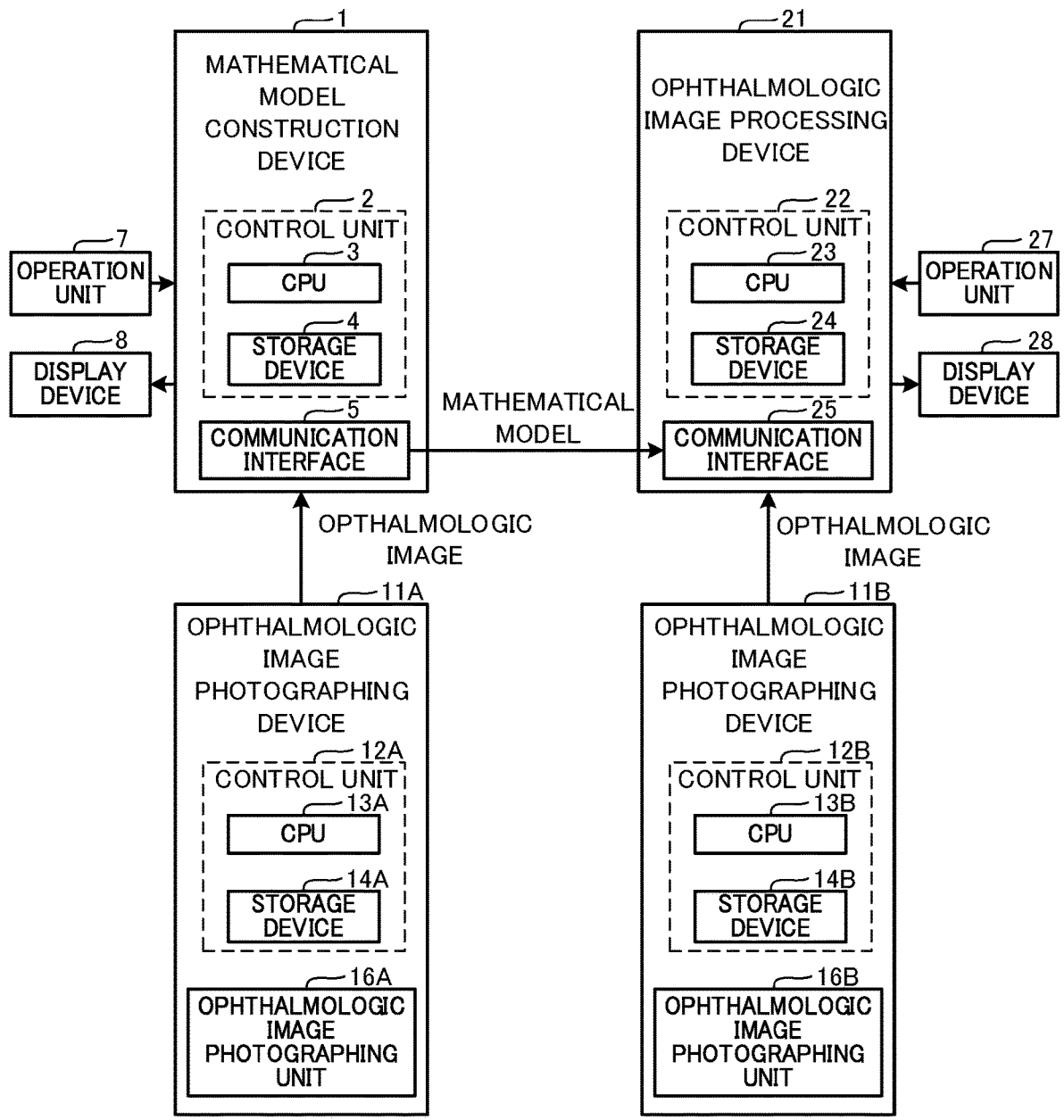
FIG. 1 is a block diagram illustrating a schematic configuration of a mathematical model construction device 1, an ophthalmologic image processing device 21, and ophthalmologic image photographing devices 11A and 11B.

A processor of an ophthalmologic image processing device exemplarily disclosed in the present disclosure acquires an ophthalmologic image photographed by an ophthalmologic image photographing device. The processor inputs the ophthalmologic image into a mathematical model trained by a machine learning algorithm and acquires a result of an analysis relating to at least one of a specific disease and a specific structure of a subject eye. The processor acquires information of a distribution of weight relating to the analysis by the mathematical model, as supplemental distribution information, for which an image area (namely, coordinates in the image area) of the ophthalmologic image input into the mathematical model is set as a variable. The processor sets a part of the image area of the ophthalmologic image, as an attention area, based on the supplemental distribution information. The processor acquires an image of a tissue including the attention area among a tissue of the subject eye and displays the image on a display unit.

In this case, a user (for example, a doctor or the like) can appropriately check the tissue in the attention area that is set based on the supplemental distribution information among the tissue of the subject eye, through the image to be displayed. For example, in a case in which the image of the tissue in an area where the weight relating to the analysis is large is displayed, the user can easily check the image of an important part where the weight is large. While, in a case in which the image of the tissue in an area where the weight is small is displayed, the user can easily check the image or the like of a part, for example, where the reliability of the analysis is low. Consequently, an operation such as a diagnosis or the like by the user can be appropriately assisted.

The ophthalmologic image photographing device that photographs the ophthalmologic image to be input into the mathematical model and the ophthalmologic image photographing device that photographs the image of the tissue including the attention area may be the identical device or different devices.

The number of the ophthalmologic images to be input into the mathematical model may be one or two or more. In a case in which a plurality of the ophthalmologic images is input into the mathematical model, the ophthalmologic images may be photographed by the identical device or different devices. Further, a dimension of the ophthalmologic image to be input into the mathematical model is not especially limited. The ophthalmologic image may be a static image or a moving image.

The number of the attention areas to be set may be one or two or more. In a case in which a plurality of the attention areas is set, an image of all of the attention areas may be displayed or an image of a certain attention area(s) (for example, the attention area selected by a user or the like) may be displayed.

The supplemental distribution information may include information (may be also called an "attention map") indicating a distribution of a degree of influence (a degree of attention) that affects the result of the analysis output by the mathematical model. In this case, the attention map is properly set in accordance with the degree of influence that affects an automatic analysis by the mathematical model.

Further, the supplemental distribution information may include information (may be also called a "certainty degree map") indicating a distribution of a degree of certainty of the analysis by the mathematical model. In this case, the attention area is properly set in accordance with the degree of certainty of the analysis by the mathematical model.

The "degree of certainty" may be defined by a highness of reliability of the analysis, or alternatively a reciprocal of a lowness of the reliability (degree of uncertainty). In a case in which the degree of uncertainty is x %, the degree of certainty may use a value of (100−x) %. Further, the "degree of certainty" denotes a degree of confidence when the mathematical model executes the analysis. The degree of certainty and accuracy of the result of the analysis are not always proportional.

A specific content of the certainty degree map can be selected as needed. For example, the degree of certainty may include the entropy of a probability distribution (average information amount) in the automatic analysis by the mathematical model. The entropy denotes unreliability, randomness, and a degree of disorder. In a case in which the degree of certainty of the automatic analysis is the maximum, the entropy of the probability distribution is zero. Further, as the degree of certainty is decreased, the entropy is increased. Accordingly, when the entropy of the probability distribution is adopted as the degree of certainty, the certainty degree map is properly generated. Further, a value other than the entropy may be adopted as the degree of certainty. For example, at least one of standard deviation, coefficient of variation, variance and the like that indicates a degree of dispersion of the probability distribution in the automatic analysis may be adopted as the degree of certainty. Kullback-Leibler divergence or the like, which is a measure of a difference between the probability distributions, may be adopted as the degree of certainty. The maximum value of the probability distribution may be adopted as the degree of certainty. Further, in a case in which ranking the diseases or the like is performed using the automatic analysis, a probability of the first rank, or a difference between the probability of the first rank and a probability of other rank (for example, a probability of the second rank or the sum of probabilities of ranks other than the first rank) may be adopted as the degree of certainty. Further, variation of outputs between the mathematical models of which data, condition, or the like used in the learning are different from each other, may be adopted as the degree of certainty. In this case, it may be adopted even if the output of the mathematical model is not the probability distribution.

In a case in which the certainty degree map is adopted as the supplemental distribution information, the processor may set an area of which the degree of certainty of the automatic analysis relating to a specific disease or a specific structure is equal to or smaller than a threshold, within the image area of the ophthalmologic image, as the attention area. In this case, an image of a part where the degree of certainty is small (namely, a part where the reliability of the analysis is low) in a specific analysis (for example, an analysis relating to a specific disease) among the tissue of the subject eye is displayed on the display unit. Accordingly, the user can check a state of the part where the degree of certainty of the analysis is small, by himself/herself using the displayed image. Consequently, an operation such as a diagnosis or the like of the user is appropriately assisted.

The processor may set an area including a position of which the weight (for example, at least one of the degree of influence and the degree of certainty) shown by the supplemental distribution information is the largest or an area of which the weight is equal to or larger than a threshold, within the image area of the ophthalmologic image, as the attention area. In this case, an image of a part where the weight in the automatic analysis is large, among the tissue of the subject eye, is displayed on the display unit. Accordingly, the user can check a state of the important part where the weight is large, by himself/herself using the displayed image. Consequently, an operation such as a diagnosis or the like of the user is appropriately assisted.

A method for setting the attention area may be modified. For example, the processor may set an area where the weight is relatively larger than other area, within the image area of the ophthalmologic image, as the attention area. Also in this case, the user can appropriately check a state of the important area where the weight is large.

The processor may display the image of the supplemental map indicating the distribution of the weight, on the display unit. The processor may set an area corresponding to an area designated by the user on the displayed supplemental map, within the image area of the ophthalmologic image input into the mathematical model, as the attention area. The processor may acquire the image of the tissue including the attention area and display the image on the display unit. In this case, the user can easily display the image of the area that the user wants to check based on the distribution of the weight, in the ophthalmologic image processing device.

The processor may acquire a tomographic image of a part passing the set attention area, among the tissue of the subject eye, and display the tomographic image on the display unit. In this case, the user can appropriately check a state of the tissue in a depth direction at the part passing the attention area, based on the displayed image. Consequently, the use can further appropriately perform the operation such as a diagnosis. Here, the tomographic image may be a two dimensional tomographic image or a three dimensional tomographic image. The tomographic image may be photographed by, for example, an OCT device or the like.

The processor may extract an image area including the attention area from the ophthalmologic image for which a tissue of the subject eye is photographed and display the image on the display unit. In this case, the use can further appropriately check a state of the tissue in the attention area based on the image for which the area including the attention area is extracted. An image from which the image area is extracted may be identical to or different from the ophthalmologic image input into the mathematical model.

Further, a display mode of the image to be displayed on the display unit based on the attention area may be modified. For example, the processor may display the ophthalmologic image for which the tissue of the subject eye is photographed, on the display unit such that image quality (for example, at least one of contrast, resolution, transparency and the like) of an image area including the attention area is set to be higher than that of an image area other than the attention area. Further, the processor may display the ophthalmologic image on the display device in a state in which the image area including the attention area is enlarged. Also in this case, the user can appropriately check a state of the tissue in the attention area. Further, the processor may display the ophthalmologic image for which the tissue of the subject eye is photographed, on the display unit in a state in which an area other than the attention area is masked.

The processor may switch whether the image of a tissue including the attention area is displayed or is not displayed on the display unit, in accordance with an instruction input by a user. In this case, the user can check a state of the tissue including the attention area at appropriate timing.

Further, even in a case in which the result of the analysis is acquired based on the ophthalmologic image without using the mathematical model trained by the machine learning algorithm, the processor can acquire the supplemental distribution information accompanied to the result of the analysis. In this case, the ophthalmologic image processing device can be represented as below. An ophthalmologic image processing device processes an ophthalmologic image of a tissue of a subject eye. The processor of the ophthalmologic image processing device: acquires the ophthalmologic image photographed by an ophthalmologic image photographing device; acquires a result of an analysis relating to at least one of a specific disease and a specific structure of the subject eye, based on the ophthalmologic image; acquires information of a distribution of weight relating to the analysis, as supplemental distribution information, for which an image area of the ophthalmologic image is set as a variable; sets a part of the image area of the ophthalmologic image, as an attention area, based on the supplemental distribution information; acquires an image of a tissue including the attention area among a tissue of the subject eye; and displays the image on a display unit.

A processor of an ophthalmologic image processing device exemplarily disclosed in the present disclosure acquires an ophthalmologic image photographed by an ophthalmologic image photographing device. The processor inputs the ophthalmologic image into a mathematical model trained by a machine learning algorithm and acquires results of analyses relating to diseases or structures of a subject eye. The processor acquires a supplemental map, for each of the results of the analyses, that indicates a distribution of weight relating to the analysis by the mathematical model, for which an image area (namely, coordinates in the image area) of the ophthalmologic image input into the mathematical model is set as a variable. The processor generates an integration map in which the supplemental maps are integrated within an identical area and displays the image on a display unit.

In this case, a user can easily recognize the distribution of the weight relating to each of the automatic analyses, from one integration map. Accordingly, a state of each of the diseases or the structures can be further appropriately recognized.

The number of the ophthalmologic image input into the mathematical model may be one or two or more. In a case in which a plurality of the ophthalmologic images is input into the mathematical model, the ophthalmologic images may be photographed by one single device or respective devices. Further, a dimension of the ophthalmologic image to be input into the mathematical model is not especially limited. The ophthalmologic image may be a static image or a moving image.

The supplemental map (may be also called an "attention map") may indicate a distribution of a degree of influence (a degree of attention) that affects the result of the analysis output by the mathematical model. In this case, the degree of influence that affects each of the automatic analyses can be appropriately recognized from the integration map.

Further, the supplemental map (may be also called a "certainty degree map") may indicate a distribution of a degree of certainty of the automatic analysis by the mathematical model. In this case, the distribution of the degree of certainty of each of the automatic analyses by the mathematical model can be appropriately represented on the integration map.

The "degree of certainty" may be defined by a highness of reliability of the analysis, or alternatively a reciprocal of a lowness of the reliability (degree of uncertainty). In a case in which the degree of uncertainty is x %, the degree of certainty may use a value of (100−x) %. Further, the "degree of certainty" denotes a degree of confidence when the mathematical model executes the analysis. The degree of certainty and accuracy of the result of the analysis are not always proportional.

A specific content of the certainty degree map can be selected as needed. For example, the degree of certainty may include the entropy of a probability distribution (average information amount) in the automatic analysis by the mathematical model. The entropy denotes uncertainty, randomness, and a degree of disorder. In a case in which the degree of certainty of the automatic analysis is the maximum, the entropy of the probability distribution is zero. Further, as the degree of certainty is decreased, the entropy is increased. Accordingly, when the entropy of the probability distribution is adopted as the degree of certainty, the certainty degree map is properly generated. Further, a value other than the entropy may be adopted as the degree of certainty. For example, at least one of standard deviation, coefficient of variation, variance and the like that indicates a degree of dispersion of the probability distribution in the automatic analysis may be adopted as the degree of certainty. Kullback-Leibler divergence or the like, which is a measure of a difference between the probability distributions, may be adopted as the degree of certainty. The maximum value of the probability distribution may be adopted as the degree of certainty. Further, in a case in which ranking the diseases or the like is performed using the automatic analysis, a probability of the first rank, or a difference between the probability of the first rank and a probability of other rank (for example, a probability of the second rank or the sum of probabilities of ranks other than the first rank) may be adopted as the degree of certainty.

The processor may change a display mode of each of the supplemental maps and integrate the supplemental maps to generate the integration map. In this case, the user can appropriately recognize each of the supplemental maps integrated into the integration map by a difference of the display modes thereof.

The display mode changed for each supplemental map may be defined by, for example, at least one of a color that shows the weight (the degree of influence, the degree of certainty, or the like), a type of a contour line, a thickness of the contour line, and the like.

In a case in which the weight (for example, the degree of influence, the degree of certainty, or the like) is shown by a color, the processor may show a magnitude of the weight using the depth of the color. In this case, the user can appropriately recognize the magnitude of the weight of each area through the depth of the color for each area.

The processor may display the integration map to be superimposed on the ophthalmologic image of the subject eye. In this case, the user can easily compare several kinds of the distributions of the weight with the distribution of the tissue of the subject eye. Consequently, the user can further properly perform the operation such as a diagnosis.

While, a method for displaying the integration map may be changed. For example, the processor may display the ophthalmologic image of the subject eye and the integration map side by side on the display unit. In this case, the processor may display the ophthalmologic image and the integration map such that image areas of them are identical to each other. In a case in which the image areas are identical to each other, the distribution of the weight and the distribution of the tissue can be compared further easily. While, the processor may display only the integration map on the display unit.

The processor may execute at least one of switching whether the integration map is displayed to be superimposed on the ophthalmologic image of the subject eye or is not displayed and changing a transparency of the integration map to be superimposed on the ophthalmologic image, in accordance with an instruction input by a user. In this case, the user can further easily compare the several kinds of the distributions of the weight with the distribution of the tissue of the subject eye. Further, the user also can check only the tissue of the subject eye by deleting the integration map displayed to be superimposed.

Further, even in a case in which the result of the analysis is acquired based on the ophthalmologic image without using the mathematical model trained by the machine learning algorithm, the processor can acquire the supplemental distribution information accompanied to the result of the analysis. In this case, the ophthalmologic image processing device can be represented as below. An ophthalmologic image processing device processes an ophthalmologic image of a tissue of a subject eye. The processor of the ophthalmologic image processing device: acquires the ophthalmologic image photographed by an ophthalmologic image photographing device; acquires results of analyses relating to diseases or structures of a subject eye, based on the ophthalmologic image; acquires a supplemental map, for each of the results of the analyses, that indicates a distribution of weight relating to the analysis, for which an image area of the ophthalmologic image is set as a variable; generates an integration map in which the supplemental maps are integrated within an identical area; and displays the integration map on a display unit.

Device Configuration

Hereinafter, one typical embodiment of the present disclosure will be described with reference to the drawings. As shown in FIG. 1, in the present embodiment, a mathematical model construction device 1, an ophthalmological image processing device 21, and ophthalmological image photographing devices 11A and 11B are used. The mathematical model construction device 1 constructs a mathematical model by training a mathematical model using a machine learning algorism. The constructed mathematical model outputs a result of an analysis relating to at least one of a specific disease and a specific structure of a subject eye, based on the input ophthalmologic image. The ophthalmologic image processing device 21 acquires the result of the analysis by using the mathematical model and acquires supplemental distribution information (the details thereof are described below) indicating a distribution of weight (for example, at least one of a distribution of a degree of influence to the automatic analysis and a distribution of a degree of certainty of the automatic analysis) having an area (coordinate) of the input image as a variable against a specific confirmation item in the automatic analysis. The ophthalmologic image processing device 21 generates various information for assisting an operation of a user (for example, a doctor or the like) based on the supplemental distribution information and provides the information to the user. Each of the ophthalmologic image photographing devices 11A and 11B photographs an ophthalmologic image of a tissue of a subject eye.

As one example, a personal computer (hereinafter, referred to as PC) is adopted as the mathematical model construction device 1 of the present embodiment. Although the details thereof are described below, the mathematical model construction device 1 trains the mathematical model by using the data of the ophthalmologic image of a subject eye (hereinafter, referred to as training ophthalmologic image) acquired from the ophthalmologic image photographing device 11A and the data indicating at least one of the disease and the structure of the subject eye of which the training ophthalmologic image is photographed. As a result, the mathematical model is constructed. However, a device served as the mathematical model construction device 1 is not limited to the PC. For example, the ophthalmologic image photographing device 11A may be served as the mathematical model construction device 1. Further, processors of several devices (for example, a CPU of the PC and a CPU 13A of the ophthalmologic image photographing device 11A) may work together to construct the mathematical model.

Further, a PC is adopted as the ophthalmologic image processing device 21 of the present embodiment. However, a device served as the ophthalmologic image processing device 21 is not limited to the PC. For example, the ophthalmologic image photographing device 11B, a server, or the like may be served as the ophthalmologic image processing device 21. In a case in which the ophthalmologic image photographing device 11B is served as the ophthalmologic image processing device 21, the ophthalmologic image photographing device 11B photographs the ophthalmologic image and then acquires the result of the analysis and the supplemental distribution information from the photographed ophthalmologic image. Further, the ophthalmologic image photographing device 11B may photograph the image of an appropriate part of a subject eye, based on the acquired supplemental distribution information. Further, a mobile terminal such as a tablet and a smartphone may be served as the ophthalmologic image processing device 21. Processors of several devices (for example, a CPU of the PC and a CPU 13B of the ophthalmologic image photographing device 11B) may work together to execute various processes.

In the present embodiment, a configuration that adopts a CPU as one example of a controller that executes various processes is exemplarily described. However, it should be obvious that a controller other than the CPU may be adopted in at least a part of each device. For example, a GPU may be adopted as the controller to accelerate the processes.

Hereinafter, the mathematical model construction device 1 is described. The mathematical model construction device 1 is arranged in, for example, a manufacturer or the like that provides a user with the ophthalmologic image processing device 21 or an ophthalmologic image processing program. The mathematical model construction device 1 is provided with a control unit 2 that executes various control processes, and a communication interface 5. The control unit 2 includes a CPU 3 served as a controller, and a storage device 4 that can store a program, a data, and the like. A mathematical model construction program for executing a mathematic model construction process (see FIG. 2) described below is stored in the storage device 4. The communication interface 5 connects the mathematic model construction device 1 to other device (for example, the ophthalmologic image photographing device 11A, the ophthalmologic image processing device 21, and the like).

The mathematical model construction device 1 is connected to an operation unit 7 and a display device 8. The operation unit 7 is operated by a user that inputs various instructions to the mathematical model construction device 1. For example, at least one of a keyboard, a mouse, a touch panel and the like may be adopted as the operation unit 7. Further, a microphone or the like may be adopted together with or instead of the operation unit 7 in order to input various instructions. The display device 8 displays various images. Various devices (for example, at least one of a monitor, a display, a projector, and the like) that can display images may be adopted as the display device 8. The "image" of the present disclosure includes both of a static image and a moving image.

The mathematical model construction device 1 acquires the data of the ophthalmologic image (hereinafter, also referred to as merely "ophthalmologic image") from the ophthalmologic image photographing device 11A. The mathematical model construction device 1 may acquire the data of the ophthalmologic image from the ophthalmologic image photographing device 11A through, for example, at least one of wired communication, wireless communication, a detachable storage medium (for example, USB memory) and the like.

Next, the ophthalmologic image processing device 21 is described. The ophthalmologic image processing device 21 is arranged in facilities (for example, hospitals, medical check facilities, or the like) that, for example, diagnose or examine a subject. The ophthalmologic image processing device 21 is provided with a control unit 22, and a communication interface 25. The control unit 22 includes a CPU 23 served as a controller and a storage device 24 that can store a program, a data, and the like. An ophthalmologic image processing program for executing an ophthalmologic image process described below (a check image display process shown in FIG. 7 and integration map display process shown in FIG. 10) is stored in the storage medium 24. The ophthalmologic image processing program includes a program that executes the mathematical model constructed by the mathematical model construction device 1. The communication interface 25 connects the ophthalmologic image processing device 21 to other device (for example, the ophthalmologic image photographing device 11B, the mathematical model construction device 1, and the like).

The ophthalmologic image processing device 21 is connected to an operation unit 27 and a display device 28. Various devices may be adopted as the operation unit 27 and the display device 28, similar to the operation unit 7 and the display device 8 described above.

The ophthalmologic image processing device 21 acquires the ophthalmologic image from the ophthalmologic image photographing device 11B. The ophthalmologic image processing device 21 may acquire the ophthalmologic image from the ophthalmologic image photographing device 11B through, for example, at least one of wired communication, wireless communication, a detachable storage medium (for example, USB memory) and the like. The ophthalmologic image processing device 21 may acquire a program or the like that executes the mathematical model constructed by the mathematical model construction device 1, through communication.

Next, the ophthalmologic image photographing devices 11A and 11B are described. As one example, in the present embodiment, a configuration that adopts the ophthalmologic image photographing device 11A that provides an ophthalmologic image to the mathematical model construction device 1 and the ophthalmologic image photographing device 11B that provides an ophthalmologic image to the ophthalmologic image processing device 21 is exemplarily described. However, the number of the ophthalmologic image photographing devices is not limited two. For example, each of the mathematical model construction device 1 and the ophthalmologic image processing device 21 may acquire an ophthalmologic image from a plurality of the ophthalmologic image photographing devices. Further, the mathematical model construction device 1 and the ophthalmologic image processing device 21 may acquire an ophthalmologic image from one ophthalmologic image photographing device.

In the present embodiment, an OCT device is exemplarily adopted as the ophthalmologic image photographing device 11 (11A, 11B). However, an ophthalmologic image photographing device other than the OCT device (for example, a scanning laser ophthalmoscope (SLO), a fundus camera, a Scheimpflug camera, a corneal endothelial cell photographing device (CEM), or the like) may be adopted.

The ophthalmologic image photographing device 11 (11A, 11B) is provided with a control unit 12 (12A, 12B) that executes various control processes, and an ophthalmologic image photographing unit 16 (16A, 16B). The control unit 12 includes a CPU 13 (13A, 13B) served as a controller, and a storage device 14 (14A, 14B) that can store a program, a data, or the like.

The ophthalmologic image photographing unit 16 includes various components necessary for photographing an ophthalmologic image of a subject eye. The ophthalmologic image photographing unit 16 of the present embodiment includes an OCT light source, a branching optical element that branches an OCT light emitted from the OCT light source into a measurement light and a reference light, a scanning unit that scans an object with the measurement light, an optical system that irradiates a subject eye with the measurement light, a light receiving element that receives a synthetic light of the light reflected by a tissue of a subject eye and the reference light, and the like.

The ophthalmologic image photographing device 11 photographs a two dimensional tomographic image and a three dimensional tomographic image of a fundus of a subject eye. Specifically, the CPU 13 scans a scanning line with the OCT light (measurement light) so as to photograph the two dimensional tomographic image of a section crossing the scanning line. The two dimensional tomographic image may be a weighted average image generated through a weighted average process applied to a plurality of tomographic images of an identical part. Further, the CPU 13 scans the tissue with the OCT light in a two dimensional manner so as to photograph the three dimensional tomographic image of the tissue. For example, the CPU 13 scans respective scanning lines of which positions are different from each other in a two dimensional region when seen from a front of the tissue, with the measurement light so as to acquire a plurality of the two dimensional tomographic images. Thereafter, the CPU 13 combines the photographed two dimensional tomographic images so as to acquire the three dimensional tomographic image. Further, the ophthalmologic image photographing device 11 of the present embodiment may photograph the two dimensional front image of the fundus of the subject eye when seen from a front (Z direction along a light axis of the measurement light). The data of the two dimensional front image may be, for example, an integrated image data in which luminance values are integrated in a depth direction at each position in an X-Y direction crossing the Z direction, an integrated value of a spectrum data at each position in the X-Y direction, a luminance data at a certain identical depth at each position in the X-Y direction, a luminance data on either of layers of the retina (for example, retina surface layer) at each position in the X-Y direction, or the like.

Automatic Analysis

One example of the automatic analysis executed by the ophthalmologic image processing device 21 is described with reference to FIG. 2 and FIG. 3. As described above, the ophthalmologic image processing device 21 executes the automatic analysis relating to at least one of the disease and the structure of the subject eye, by using the mathematical model. As one example, in the present embodiment, the automatic analysis relating to the disease of the subject eye (namely, automatic diagnosis) is exemplarily described. A kind of the disease to the automatic analysis is applied can be selected as needed. The ophthalmologic image processing device 21 of the present embodiment automatically analyses presence/absence of each of the diseases including age-related macular degeneration and diabetic retinopathy, by inputting the ophthalmologic image into the mathematical model.

Figure 2:
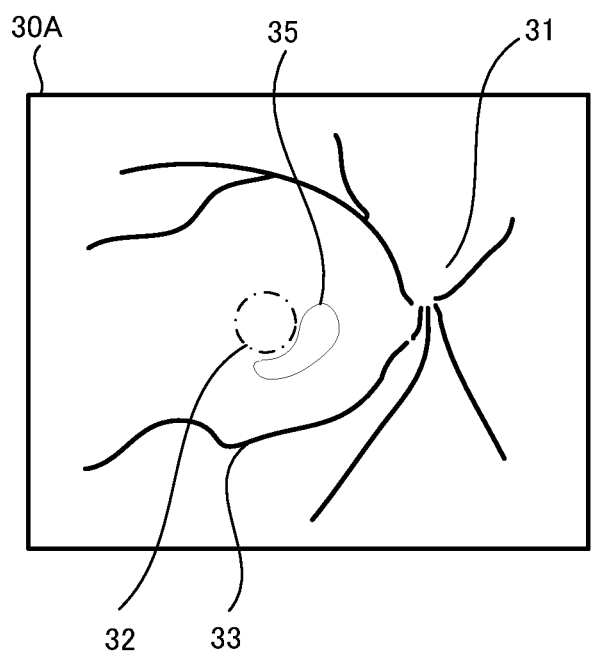
FIG. 2 illustrates one example of a front image of a fundus suffering from age-related macular degeneration.

FIG. 2 illustrates one example of a front image of a fundus suffering from the age-related macular degeneration. In an ophthalmologic image 30A exemplarily shown in FIG. 2, a lesion 35 due to the age-related macular degeneration is found in an optic papilla 31, the macula 32, and fundus blood vessels 33 of the fundus and near a macula 32 as well. The mathematical model is trained in advance by the data (input training data) of the ophthalmologic image 30A exemplarily shown in FIG. 2 and the data (output training data) indicating that the disease of the subject eye for which the ophthalmologic image 30A has been photographed, is the age-related macular degeneration. Accordingly, when the ophthalmologic image similar to the illustration shown in FIG. 2 is input into the mathematical model, a result of the automatic analysis indicating that the subject eye is likely suffering from the age-related macular degeneration, is output.

Figure 3:
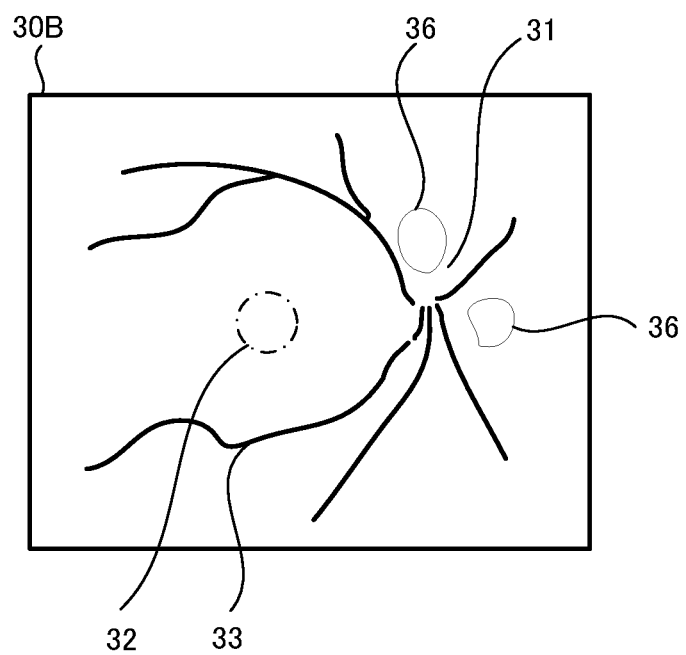
FIG. 3 illustrates one example of a front image of a fundus suffering from diabetic retinopathy.

FIG. 3 illustrates one example of a front image of a fundus suffering from the diabetic retinopathy. In an ophthalmologic image 30B exemplarily shown in FIG. 3, a lesion 36 due to the diabetic retinopathy is found in the optic papilla 31, the macula 32, and the fundus blood vessels 33 of the fundus and near the fundus blood vessels 33 as well. The mathematical model is trained in advance by the data (input training data) of the ophthalmologic image 30B exemplarily shown in FIG. 3 and the data (output training data) indicating that the disease of the subject eye for which the ophthalmologic image 30B has been photographed, is the diabetic retinopathy. Accordingly, when the ophthalmologic image similar to the illustration shown in FIG. 3 is input into the mathematical model, a result of the automatic analysis indicating that the subject eye is likely suffering from the diabetic retinopathy, is output.

Here, with the mathematical model of the present embodiment, the automatic analysis relating to a plurality of diseases is executed to one ophthalmologic image. Accordingly, a plurality of the diseases (for example, the age-related macular degeneration and the diabetic retinopathy) may be automatically determined as possible diseases.

Further, the ophthalmologic image processing device 21 may execute the automatic analysis relating to the structure (for example, at least one of a layer, a macula, an optic papilla, and a fundus blood vessel of the fundus) of the subject eye instead of or together with the automatic analysis relating to the disease. Specifically, the ophthalmologic image processing device 21 may execute the automatic analysis relating to a specific layer or a boundary of the specific layer in the fundus of the subject eye, by inputting the tomographic image (at least one of the two dimensional tomographic image and the three dimensional tomographic image) into the mathematical model. Further, the ophthalmologic image processing device 21 may execute the automatic analysis relating to a structure of a tissue (for example, at least one of the macula and the optic papilla) of the subject eye, by inputting the front image or the tomographic image of the fundus into the mathematical model. Further, the ophthalmologic image processing device 21 may execute the automatic analysis relating to the fundus blood vessels of the subject eye, by inputting the front image or the tomographic image of the fundus into the mathematical model. In this case, the ophthalmologic image processing device 21 may execute the automatic analysis relating to an artery and a vein of the fundus of the subject eye.

Supplemental Distribution Information

One example of the supplemental distribution information is described with reference to FIG. 4 and FIG. 5. In the present embodiment, the ophthalmologic image of the two dimensional image is input into the mathematical model. Thus, the supplemental distribution information is also the two dimensional information (map). However, for example, the ophthalmologic image of the three dimensional image may be input into the mathematical model. In such a case, the supplemental distribution information is the three dimensional information.

In the present embodiment, at least one of an attention map and a certainty degree map is adopted as the supplemental distribution information (supplemental map).

The attention map is a distribution of a degree of influence (a degree of attention) to respective positions within an image area, that affects the result of the analysis output by the mathematical model. An area with a large degree of influence strongly affects the result of the automatic analysis, compared to an area with a small degree of influence. One example of the attention map is disclosed in, for example, the document described below.

Ramprasaath R. Selvaraju, et al., "Grad-CAM: Visual Explanations from Deep Networks via Gradient-based Localization" Proceedings of the IEEE International Conference on Computer Vision, 2017-Oct, pp. 618-626.

The certainty degree map is a distribution of a degree of certainty of the automatic analysis at respective pixels within the image area when the mathematical model executes the automatic analysis. The degree of certainty may be defined by a highness of reliability of the automatic analysis, or alternatively a reciprocal of a lowness of the reliability (degree of uncertainty). For example, in a case in which the degree of uncertainty is x %, the degree of certainty may use a value of (100−x) %. As one example, in the present embodiment, the entropy of a probability distribution (average information amount) in the automatic analysis is adopted as the degree of certainty. In a case in which the degree of certainty of the automatic analysis is the maximum, the entropy of the probability distribution is zero. Further, as the degree of certainty is decreased, the entropy is increased. Accordingly, for example, when a reciprocal of the entropy of the probability distribution or the like is adopted as the degree of certainty, the certainty degree map is properly generated. However, information other than the entropy of the probability distribution (for example, standard deviation, coefficient of variation, variance or the like of the probability distribution) may be used for generating the certainty degree map. In a case in which the probability distribution in the automatic analysis is adopted as the degree of certainty, the probability distribution may be defined by a probability distribution in the automatic analysis for each pixel, or a probability distribution having one or more dimensional coordinates as a variable. Further, in a case in which ranking is performed using the automatic analysis, a probability of the first rank, or a difference between the probability of the first rank and a probability of other rank (for example, a probability of the second rank or the sum of probabilities of ranks other than the first rank) may be adopted as the degree of certainty.

Figure 4:
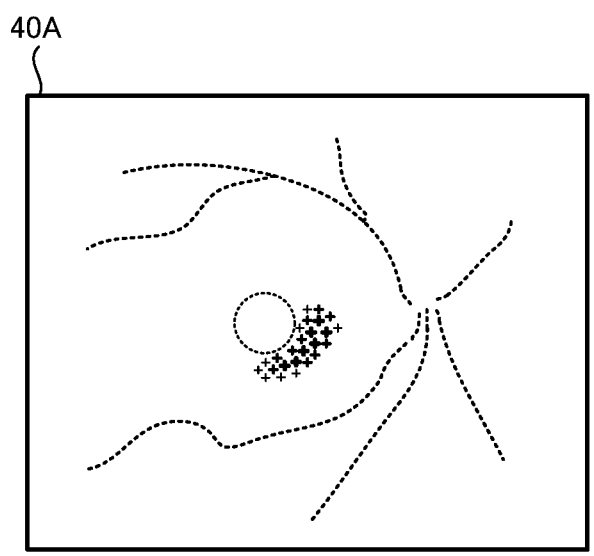
FIG. 4 illustrates one example of a supplemental map 40A in a case in which an ophthalmologic image 30A shown in FIG. 2 is subjected to an automatic analysis.

FIG. 4 illustrates one example of a supplemental map 40A in a case in which the automatic analysis based on the mathematical model is executed to the ophthalmologic image 30A shown in FIG. 2. In FIG. 4, a tissue of the fundus blood vessels 33 and the like in the ophthalmologic image 30A (see FIG. 2) is schematically illustrated by a dotted line in order for facilitating comparison between an image area of the ophthalmologic image 30A and an area of the supplemental map 40A. In the supplemental map 40A shown in FIG. 4, a magnitude of the weight (the degree of influence or the degree of certainty in the present embodiment) at each position relating to the result of the automatic analysis indicating that the probability of the age-related macular degeneration is high, is shown by the depth of a color. That is, in a part with a deep color, the degree of influence or the degree of certainty relating to the result of the automatic analysis is large, compared to a part with a light color (in FIG. 4 and FIG. 5, the depth of the color is represented by the thickness of a line of the illustration for convenience of the description). In the example shown in FIG. 4, the degree of influence or the degree of certainty in the lesion 35 (see FIG. 2) is large. Further, the degree of influence or the degree of certainty of the center in the lesion 35 is larger than that of a peripheral part in the lesion 35.

Figure 5:
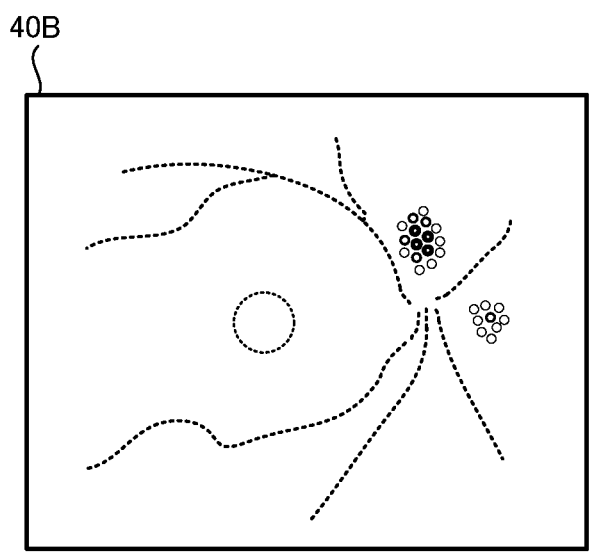
FIG. 5 illustrates one example of a supplemental map 40B in a case in which an ophthalmologic image 30B shown in FIG. 3 is subjected to an automatic analysis.

FIG. 5 illustrates one example of a supplemental map 40B in a case in which the automatic analysis based on the mathematical model is executed to the ophthalmologic image 30B shown in FIG. 3. In FIG. 5, similar to FIG. 4, a tissue of the fundus blood vessels in the ophthalmologic image 30B (see FIG. 3) and the like is schematically illustrated by a dotted line. In the supplemental map 40B shown in FIG. 5, a magnitude of the degree of influence or the degree of certainty at each position relating to the result of the automatic analysis indicating that the probability of the diabetic retinopathy is large, is shown by the depth of a color. In a part with a deep color, the degree of influence or the degree of certainty relating to the result of the automatic analysis is large. Also in the example shown in FIG. 5, the degree of influence or the degree of certainty in the lesion 35 (see FIG. 3) is large.

In each of the supplemental maps 40A and 40B of the present embodiment, a display mode of the degree of influence or the degree of certainty is changed in accordance with the disease or the structure to which the automatic analysis is applied. In the present embodiment, a color indicating the degree of influence or the degree of certainty is changed in accordance with the disease or the structure to which the automatic analysis is applied. However, a specific display mode of the supplemental map may be changed. For example, a contour line linking the positions having the same magnitude of the degree of influence or the degree of certainty may be generated to display the magnitude of the degree of influence or the degree of certainty. In this case, at least one of a color, a type, a thickness and the like of the line forming the contour line may be changed in accordance with the disease or the structure to which the automatic analysis is applied.

In the present embodiment, when the ophthalmologic image is input into the mathematical model, the mathematical model outputs both of the result of the automatic analysis of the ophthalmologic image and the supplemental distribution information (the supplemental map in the present embodiment) accompanied to the automatic analysis. However, a method for generating the supplemental distribution information may be changed. For example, the CPU 23 of the ophthalmologic image processing device 21 may generate the supplemental distribution information based on the result of the automatic analysis output by the mathematical model.

In the present embodiment, a configuration in which the automatic analysis is executed to the disease of the subject eye is exemplarily described. However, also in a case in which the automatic analysis is execute to the structure of the subject eye, the supplemental distribution information similar to that described above may be generated. For example, in a case in which the automatic analysis is executed to an artery and a vein of the fundus of the subject eye, the supplemental distribution information to a result of the automatic analysis relating to the artery and the supplemental distribution information to a result of the automatic analysis relating to the vein may be generated. In this case, regarding a part having a small degree of certainty of the automatic analysis relating to the artery and the vein among the fundus blood vessels, the supplemental distribution information indicating the blood vessel having a small degree of certainty may be generated.

Mathematical Model Construction Process

A mathematical model construction process executed by the mathematical model construction device 1 is described with reference to FIG. 6. The mathematical model construction process is executed by the CPU 3 in accordance with the mathematical model construction program stored in the storage device 4. In the mathematical model construction process, the mathematical model is trained by a training data set, so that the mathematical model for executing the automatic analysis relating to the disease or the structure of the subject eye is constructed. The training data set includes an input data (input training data) and an output data (output training data).

Figure 6:
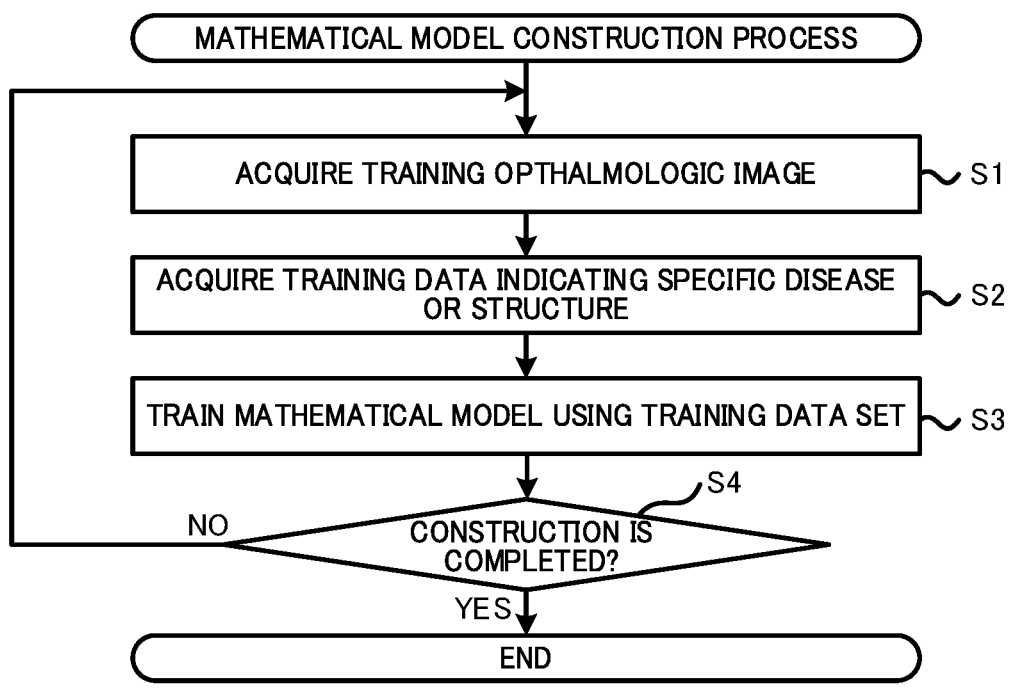
FIG. 6 is a flowchart illustrating a mathematical model construction process executed by the mathematical model construction device 1.

As shown in FIG. 6, the CPU 3 acquires the data of the training ophthalmologic image, which is an ophthalmologic image photographed by the ophthalmologic image photographing device 11A, as the input training data (S1). In the present embodiment, the data of the training ophthalmologic image is generated by the ophthalmologic image photographing device 11A and then acquired by the mathematical model construction device 1. However, the CPU 3 may acquire the data of the training ophthalmologic image by acquiring a signal (for example, OCT signal), which is a basis for generating the training ophthalmologic image, from the ophthalmologic image photographing device 11A, and then generating the ophthalmologic image based on the acquired signal.

In S1 of the present embodiment, a two dimensional front image (so-called Enface image) of a fundus photographed by the ophthalmologic image photographing device 11A served as the OCT device is acquired as the training ophthalmologic image. However, the training ophthalmologic image may be photographed by a device other than the OCT device (for example, at least one of an SLO device, a fundus camera, an infrared camera, a corneal endothelial cell photographing device and the like). Further, the training ophthalmologic image is not limited to a two dimensional front image of a fundus. For example, a two dimensional tomographic image or a three dimensional tomographic image may be acquired as the training ophthalmologic image. Or alternatively, a moving image may be acquired as the training ophthalmologic image.

Next, the CPU 3 acquires the data indicating at least one of the disease and the structure (disease in the present embodiment) of the subject eye for which the training ophthalmologic image is photographed, as the output training data (S2). As one example, in the present embodiment, an operator (for example, a doctor or the like) diagnoses the disease by checking the training ophthalmologic image and inputs a kind of the disease if applicable, into the mathematical model construction device 1 by operating the operation unit 7, so that the output training data is generated. The output training data may include the data indicating a position of the lesion in addition to the data of presence/absence of the disease and a kind of the disease.

The output training data may be modified. For example, in a case in which the automatic analysis is executed to the structure of the subject eye using the mathematical model, the data indicating a position of a specific structure (for example, at least one of a position of a layer, a position of a boundary, a position of a specific tissue and the like) in the training ophthalmologic image may be adopted as the output training data.

Next, the CPU 3 trains the mathematical model using the training data set by the machine learning algorithm (S3). As the machine learning algorithm, for example, a neural network, a random forest, a boosting, a support vector machine (SVM), and the like are generally known.

The neural network is a technique that imitates the behavior of a neuron network of a living organism. Examples of the neural network include a feedforward neural network, a radial basis function (RBF) network, a spiking neural network, a convolutional neural network, a recurrent neural network (a recurrent neural network, a feedback neural network, and the like), a probabilistic neural network (a Boltzmann machine, a Bayesian network, and the like).

The random forest is a method to generate multiple decision trees, by performing learning on the basis of training data that is randomly sampled. When the random forest is used, branches of a plurality of the decision trees learned in advance as discriminators are followed, and an average (or a majority) of results obtained from the decision trees is calculated.

The boosting is a method to generate a strong discriminator by combining a plurality of weak discriminators. By causing sequential learning of simple and weak discriminators, the strong discriminator is constructed.

The SVM is a method to configure two-class pattern discriminators using linear input elements. For example, the SVM learns linear input element parameters from training data, using a reference (a hyperplane separation theorem) that calculates a maximum margin hyperplane at which a distance from each of data points is the maximum.

The mathematical model indicates, for example, a data structure for predicting a relationship between input data (the data of the two dimensional front image similar to the training ophthalmologic image in the present embodiment) and output data (the data of the result of the automatic analysis relating to the disease in the present embodiment). The mathematical model is constructed as a result of training using the training data set. As described above, the training data set is a set of the input training data and the output training data. For example, as a result of the training, correlation data (for example, weight) between the inputs and outputs is updated. The mathematical model in the present embodiment is trained to output the result of the automatic analysis, and the supplemental distribution information (the supplemental map in the present embodiment) accompanied to the automatic analysis as well.

In the present embodiment, a multi-layer neural network is adopted as the machine learning algorithm. The neural network includes an input layer for inputting data, an output layer for generating the data of the result of the automatic analysis to be predicted, and one or more hidden layers between the input layer and the output layer. A plurality of nodes (also known as units) is arranged in each of the layers. Specifically, a convolutional neural network (CNN) that is a type of the multi-layer neural network is adopted in the present embodiment.

Here, other machine learning algorithm may be adopted. For example, generative adversarial networks (GAN) using two competitive neural networks may be adopted as the machine learning algorithm.

The processes of S1 to S3 are repeated until the construction of the mathematical model is completed (S4: NO). That is, the mathematical model is repeatedly trained by the multiple training data sets including the training data set of the subject eye suffering from a disease (for example, see FIG. 2 and FIG. 3) and the training data set of the subject eye not suffering from a disease. When the construction of the mathematical model is completed (S4: YES), the mathematical model construction process is finished. The program and the data that execute the constructed mathematical model are installed in the ophthalmologic image processing device 21.

Check Image Display Process

A check image display process executed by the ophthalmologic image processing device 21 is described with reference to FIG. 7 to FIG. 9. A check image denotes an image suitable for a user to check it directly. In the present embodiment, the check image is automatically acquired based on the supplemental distribution information. The check image display process is executed by the CPU 23 in accordance with the ophthalmologic image processing program stored in the storage device 24.

Firstly, the CPU 23 acquires the ophthalmologic image of the subject eye (S11). It is preferable that a kind of the ophthalmologic image acquired in S11 is similar to the ophthalmologic image used as the input training data in the mathematical model construction process (see FIG. 6) described above. As one example, in S11 of the present embodiment, the two dimensional front image of the fundus of the subject eye is acquired. The CPU 23 may acquire a signal (for example, OCT signal), which is a basis of the ophthalmologic image, from the ophthalmologic image photographing device 11B and generate the ophthalmologic image based on the acquired signal.

The CPU 23 inputs the acquired ophthalmologic image into the mathematical model and acquires the result of the automatic analysis output by the mathematical model (S12). As described above, in the present embodiment, the results of the automatic analyses relating to the specific respective diseases are output by the mathematical model.

The CPU 23 acquires the supplemental distribution information accompanied to the automatic analysis in S12 (S13). As described above, in the present embodiment, at least one of the attention map and the certainty degree map is acquired as the supplemental distribution information (supplemental map). Further, in the present embodiment, the mathematical model outputs both of the result of the automatic analysis and the supplemental distribution information. However, the CPU 23 may generate the supplemental distribution information based on the result of the automatic analysis.

Next, the CPU 23 sets an attention area in a part of the image area of the ophthalmologic image acquired in S11, based on the supplemental distribution information (S16). Specifically, in a case in which the certainty degree map is acquired as the supplemental distribution information, the ophthalmologic image processing device 21 of the present embodiment displays an image of a part where the degree of certainty is small (namely, in the present embodiment, a part where the reliability of the automatic analysis relating to a specific disease is considered to be low), on the display device 28. In this case, a user can check a state of the part where the degree of certainty of the specific automatic analysis is small, by himself/herself using the check image to be displayed. Further, the ophthalmologic image processing device 21 of the present embodiment displays an image of a part where the weight (at least one of the degree of influence and the degree of certainty) shown by the supplemental distribution information is large, on the display device 28. In this case, a user can appropriately check a state of the important part where the weight is large (namely in the present embodiment, a state of the part where the possibility of a specific disease is determined high), based on the check image. The user operates the operation unit 27 so as to input either of an instruction to display the part where the degree of certainty is small and an instruction to display the part where the degree of influence or the degree of certainty is large, into the ophthalmologic image processing device 21.

In a case in which the instruction to display the part where the degree of certainty is small is input, the CPU 23 sets an area where the degree of certainty shown by the supplemental distribution information (specifically, the certainty degree map) is equal to or smaller than a threshold, as the attention area (S16). That is, the CPU 23 sets the area where the degree of certainty of the automatic analysis relating to a specific disease or structure (a specific disease in the present embodiment) is equal to or smaller than the threshold, as the attention area.

A specific content of the process for setting the attention area may be selected as needed. As one example, as shown in FIG. 8, the CPU 23 of the present embodiment separately extracts continuous areas where the degrees of certainty in the automatic analysis relating to the specific disease or structure are equal to or larger than a first threshold, respectively. In an example shown in FIG. 8, two areas 46A and 46B where the degrees of certainty are equal to or larger than the first threshold, are extracted. Thereafter, the CPU 23 sets an area where the maximum value of the degree of certainty is equal to or smaller than a second threshold (second threshold>first threshold) within the extracted area, as the attention area. In the example shown in FIG. 8, since the maximum value of the degree of certainty of the area 46A is larger than the second threshold, it is considered that the reliability of the automatic analysis relating to the specific disease is high. While, since the maximum value of the degree of certainty of the area 46B is equal to or smaller than the second threshold, it is considered that the reliability of the automatic analysis relating to the specific disease is low. Accordingly, in the example shown in FIG. 8, among two areas 46A and 46B, the area 46B where the maximum value of the degree of certainty is equal to or smaller than the second threshold is set as an attention area 48. In this case, among the areas 46A and 46B analyzed as likely suffering from the specific disease, only the area where the reliability of the automatic analysis is lower is set as the attention area.

The content of the process for setting the attention area may be modified. For example, the CPU 23 may set all areas where the degrees of certainty are in a range between the first threshold and the second threshold, as the attention area. The first threshold may be set as needed to the value larger than zero in accordance with various conditions.

Further, in a case in which the instruction to display the part where the weight (the degree of influence or the degree of certainty in the present embodiment) is large is input, the CPU 23 sets the area including a position where the weight shown by the supplemental distribution information (specifically, at least one of the attention map and the certainty degree map) is the largest, as the attention area (S16). For example, in the example shown in FIG. 8, the position where the degree of influence or the degree of certainty is the largest exists in the area 46A. Accordingly, the CPU 23 sets the area 46A as the attention area. Also, in a case in which the instruction to display the part where the weight is large is input, the content of the process in S16 may be modified. For example, the CPU 23 may set an area where the weight (the degree of influence or the degree of certainty) is equal to or larger than a threshold, as the attention area. Further, the CPU 23 may set an area where the weight is relatively larger than other area, as the attention area. Further, the attention area having a specific size may be set such that the accumulated value of the weight in the area is the largest. Further, two or more attention areas may be set.

Next, the CPU 23 acquires the image of a tissue including the attention area among the tissue of the subject eye, as the check image (S18). As one example, the CPU 23 of the present embodiment acquires a tomographic image of a part passing the attention area among the tissue of the subject eye, as the check image.

Figure 9:
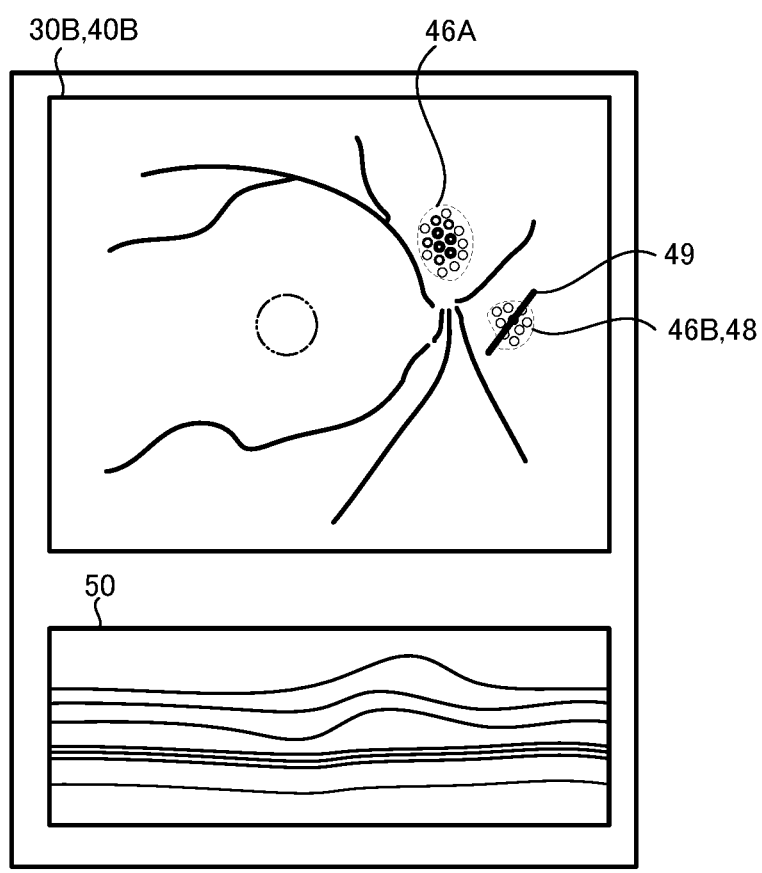
FIG. 9 illustrates one example of a display screen of a display device 28 displaying the ophthalmologic image 30B, the supplemental map 40B, and a check image 50.

FIG. 9 illustrates one example of a display screen of the display device 28 displaying the ophthalmologic image 30B, the supplemental map 40B, and a check image 50. In an example shown in FIG. 9, the supplemental map 40B is displayed to be superimposed on the ophthalmologic image 30B, which is input into the mathematical model, in a state in which the areas are matched with each other. Accordingly, a user can appropriately check the distribution of the weight accompanied to the automatic analysis, on the ophthalmologic image 30B.

In the example shown in FIG. 9, the CPU 23 sets a line 49 indicating a position of the tomographic image to be acquired on the two dimensional attention area 48 and displays the line 49 on the display device 28. In the example shown in FIG. 9, one straight line 49 is set to cross the attention area 48. However, the line is not limited to a straight line. Further, a plurality of the lines may be set. Further, a two dimensional area indicating a position of the tomographic image to be acquired may be set instead of the line. The CPU 23 acquires the two dimensional tomographic image 50 on a section crossing a tissue in a depth direction at a position of the set line and displays it on the display device 28. In a case in which the two dimensional area indicating the position of the tomographic image to be acquired is set, the CPU 23 acquires a three dimensional tomographic image extended from the set two dimensional area in the depth direction of a tissue and displays it on the display device 28. The CPU 23 may acquires the tomographic image corresponding to the set line or the set area, from the two dimensional tomographic image or the three dimensional tomographic image photographed in advance by the ophthalmologic image photographing device 11B. Further, the CPU 23 may output an instruction to photograph the tomographic image corresponding to the set line or the set area, to the ophthalmologic image photographing device 11B.

In S16 of the present embodiment, the attention area is automatically set based on the supplemental distribution information. However, the attention area may be set based on the instruction input by a user. For example, as shown in FIG. 9, the CPU 23 may urge a user to designate the attention area on the supplemental map 40B in a state in which the supplemental map 40B is displayed on the display device 28. The CPU 23 may set the area corresponding to the area designated by a user on the supplemental map 40B within the image area in the ophthalmologic image 30B, as the attention area.

The CPU 23 of the present embodiment may display an image other than the tomographic image, as the check image. For example, the CPU 23 may extract an image area including the attention area from the ophthalmologic image for which a tissue of a subject eye is photographed, as the check image. In this case, the ophthalmologic image, which is the basis of the check image to be extracted, may be identical to or different from each of the ophthalmologic images 30A and 30B to be input into the mathematical model. The ophthalmologic image, which is the basis of the check image to be extracted, may be a two dimensional image or a three dimensional image.

Further, the CPU 23 may display the ophthalmologic image for which a tissue of a subject eye is photographed, on the display device 28 such that the picture quality of the image area including the attention area is set to be higher than that of the other area. Further, the CPU 23 may display the ophthalmologic image for which a tissue of a subject eye is photographed, on the display device 28 in a state in which the image area including the attention area is enlarged. Further, the CPU 23 may display the ophthalmologic image on the display device 28 in a state in which an area other than the attention area is masked.

Next, the CPU 23 determines whether the instruction to display the check image is input by a user (S20). In the present embodiment, a user may input an instruction to display or not to display the check image on the display device 28, through the operation unit 27. In a case in which the instruction to display the image is input (S20: YES), the CPU 23 displays the check image on the display device 28. While, in a case in which the instruction not to display the image is input (S20: NO), the CPU 23 does not display the check image (S22). The processes S20 to S23 are repeated until an instruction to finish the process is input (S23: NO). When the instruction to finish the process is input (S23: YES), the check image display process is finished.

Figure 8:
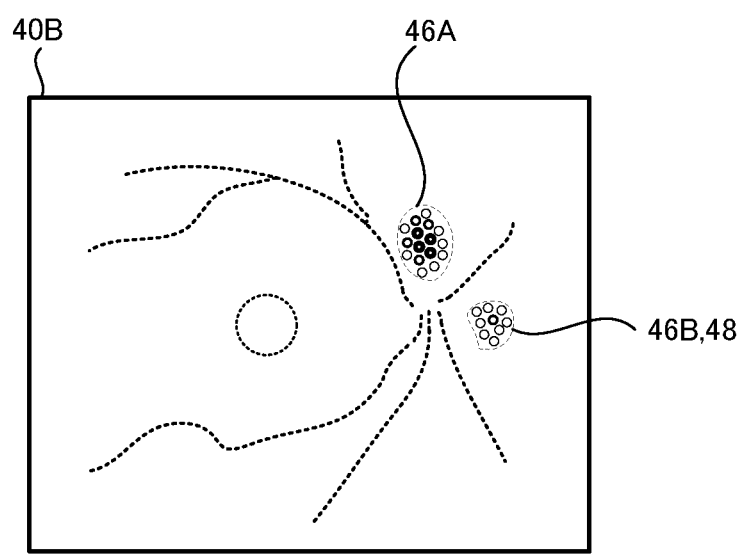
FIG. 8 illustrates one example of a method for setting areas 46A, 46B and 48 based on the supplemental map 40A.

In each of FIG. 8 and FIG. 9, a configuration in which only the result of the automatic analysis relating to the diabetic retinopathy, which is one of the diseases and structures, is output is exemplarily described. However, as described above, according to the mathematical model of the present embodiment, the automatic analysis relating to a plurality of the diseases is executed to one ophthalmologic image. In a case in which the results of the automatic analyses relating to a plurality of the diseases and structures are output, the process that displays the check image may be executed for one result of the automatic analysis, or alternatively may be executed for each of the results of the automatic analyses. Further, the process that displays the check image may be executed for a result of the automatic analysis selected by a user among the results of the automatic analyses.

Integration Map Display Process

Figure 11:
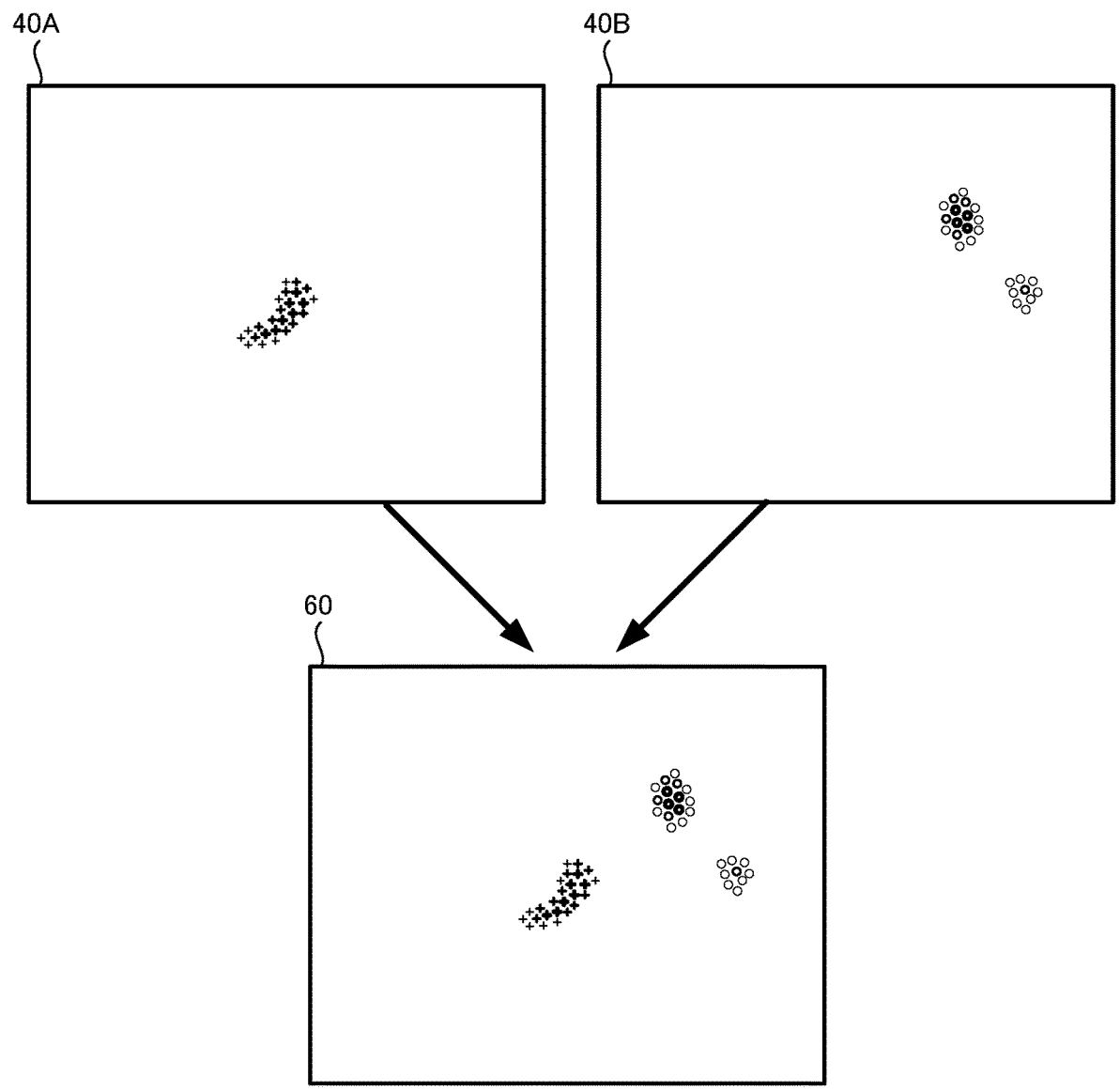
FIG. 11 illustrates one example of a method for generating an integration map 60 by integrating two supplemental maps 40A and 40B.
Figure 12:
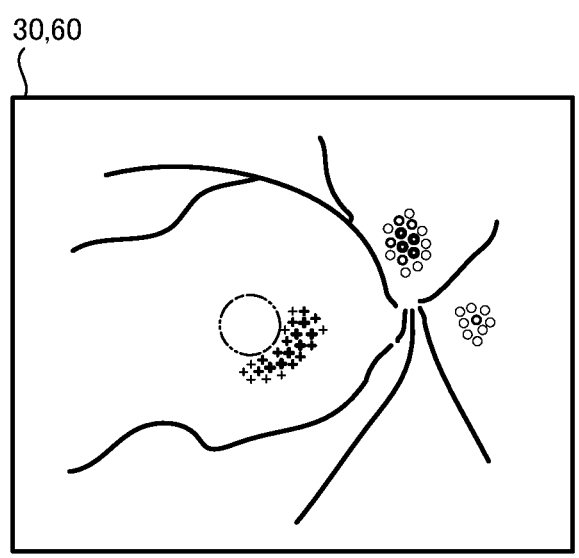
FIG. 12 illustrates one example of the ophthalmologic image 30 on which the integration map 60 is superimposed.

An integration map display process executed by the ophthalmologic image processing device 21 is described with reference to FIG. 10 to FIG. 12. An integration map denotes a map generated by integrating multiple supplemental maps accompanied to respective results of the automatic analyses. With the integration map, a distribution of the weight (the degree of influence or the degree of certainty in the present embodiment) relating to each of the results of the automatic analyses is recognized easily. The integration map display process is executed by the CPU 23 in accordance with the ophthalmologic image processing program stored in the storage device 21.

Firstly, the CPU 23 acquires the ophthalmologic image of a subject eye (S31). As the process of S31, a process similar to that of S11 described above (see FIG. 7) may be adopted. Next, the CPU 23 inputs the acquired ophthalmologic image into the mathematical model and acquires the results of the automatic analyses relating to diseases and structures (S32). As described above, in the present embodiment, the results of the automatic analyses respectively relating to the specific diseases are output by the mathematical model.

The CPU 23 acquires the supplemental maps respectively accompanied to the automatic analyses in S32 (S33). As described above, in the present embodiment, at least one of the attention map and the certainty degree map is acquired as the supplemental map.

The CPU 23 generates the integration map by integrating the supplemental maps acquired in S33, within the identical area (S34). FIG. 11 illustrates one example of a method for generating an integration map 60 by integrating the two supplemental maps 40A and 40B (see FIG. 4 and FIG. 5). The CPU 23 generates one integration map 60 by integrating the supplemental maps (in the example shown in FIG. 11, two supplemental maps 40A and 40B), within the identical area. Specifically, the CPU 23 of the present embodiment integrates the supplemental maps 40A and 40B by changing a display mode for each of the supplemental maps 40A and 40B. In the example shown in FIG. 11, the CPU 23 changes the color indicating the degree of influence or the degree of certainty is changed for each of the supplemental maps 40A and 40B. However, the CPU 23 may change the display mode other than the color for each of the supplemental maps.

Next, the CPU 23 determines whether the instruction to display the integration map 60 to be superimposed on the ophthalmologic image 30 is input (S36). In the present embodiment, a user may input an instruction whether the integration map 60 is superimposed on the ophthalmologic image 30, through the operation unit 27. In a case in which the instruction to display the integration map 60 to be superimposed is not input (S36: NO), the CPU 23 does not display the integration map 60 to be superimposed on the ophthalmologic image 30 (S37). In a case in which the instruction to display the integration map 60 to be superimposed is input (S36: YES), the CPU 23 displays the integration map 60 to be superimposed on the ophthalmologic image 30 of a subject eye as shown in FIG. 12 (S38). Accordingly, a user can easily compare a plurality of kinds of the distributions of the degree of influence or the degree of certainty with the distribution of a tissue of a subject eye.

Next, the CPU 23 determines whether an instruction to change the transparency of the integration map 60 superimposed and displayed on the ophthalmologic image 30 (S39). In the present embodiment, a user may operate the operation unit 27 to designate the transparency of the integration map 60. In a case in which the instruction to change the transparency is input (S39: YES), the CPU 23 changes the transparency of the integration map 60, which is superimposed and displayed on the ophthalmologic image 30, into the instructed transparency (S40). Accordingly, a user can further properly compare the distributions of a plurality of kinds of the weight (the degree of influence or the degree of certainty) with the distribution of a tissue of a subject eye. The processes S36 to S42 are repeated until an instruction to finish the process (S42: NO). When the instruction to finish the process is input (S42: YES), the integration map display process is finished.

The technology disclosed in the above-described embodiment is merely an example. Thus, the technique exemplarily described in the embodiment described above may be modified. For example, in the embodiment described above, a configuration in which the automatic analysis is executed to each of the diseases is exemplarily described. Also in a configuration in which the automatic analysis is executed each of structures of a subject eye, the process similar to that described above may be executed. For example, in a case in which an automatic analysis is executed to an artery and a vein of a fundus of a subject eye, a supplemental map accompanied to a result of the automatic analysis relating to the artery and a supplemental map accompanied to a result of the automatic analysis relating to the vein may be integrated so as to generate the integration map. In this case, a part with high reliability and a part with low reliability of the analyses relating to the artery and the vein are easily recognized through the integration map.

Further, in the embodiment described above, the two dimensional supplemental map and the integration map are displayed on the display device 28. However, the CPU 23 may acquire a three dimensional supplemental map and display it on the display device 28. Further, the CPU 23 may generate the integration map by integrating a plurality of the three dimensional supplemental maps and display it on the display device 28.

Further, in the embodiment described above, the mathematical model trained by the machine learning algorithm is used for acquiring the result of relating to at least one of a specific disease and a specific structure. However, even in a case in which the result of the analysis is automatically acquired based on the ophthalmologic image without using the mathematical model trained by the machine learning algorithm, the CPU 23 can acquire the supplemental distribution information accompanied to the automatic analysis. Also in this case, similar to the embodiment described above, the CPU 23 may set the attention area based on the supplemental distribution information and display the image of a tissue including the attention area on the display device 28. Further, when the CPU 23 acquires a plurality of the results of the automatic analyses without using the machine learning algorithm, the CPU 23 may acquire the supplemental maps accompanied to the respective automatic analyses and generate the integration map by integrating the supplemental maps.

Figure 7:
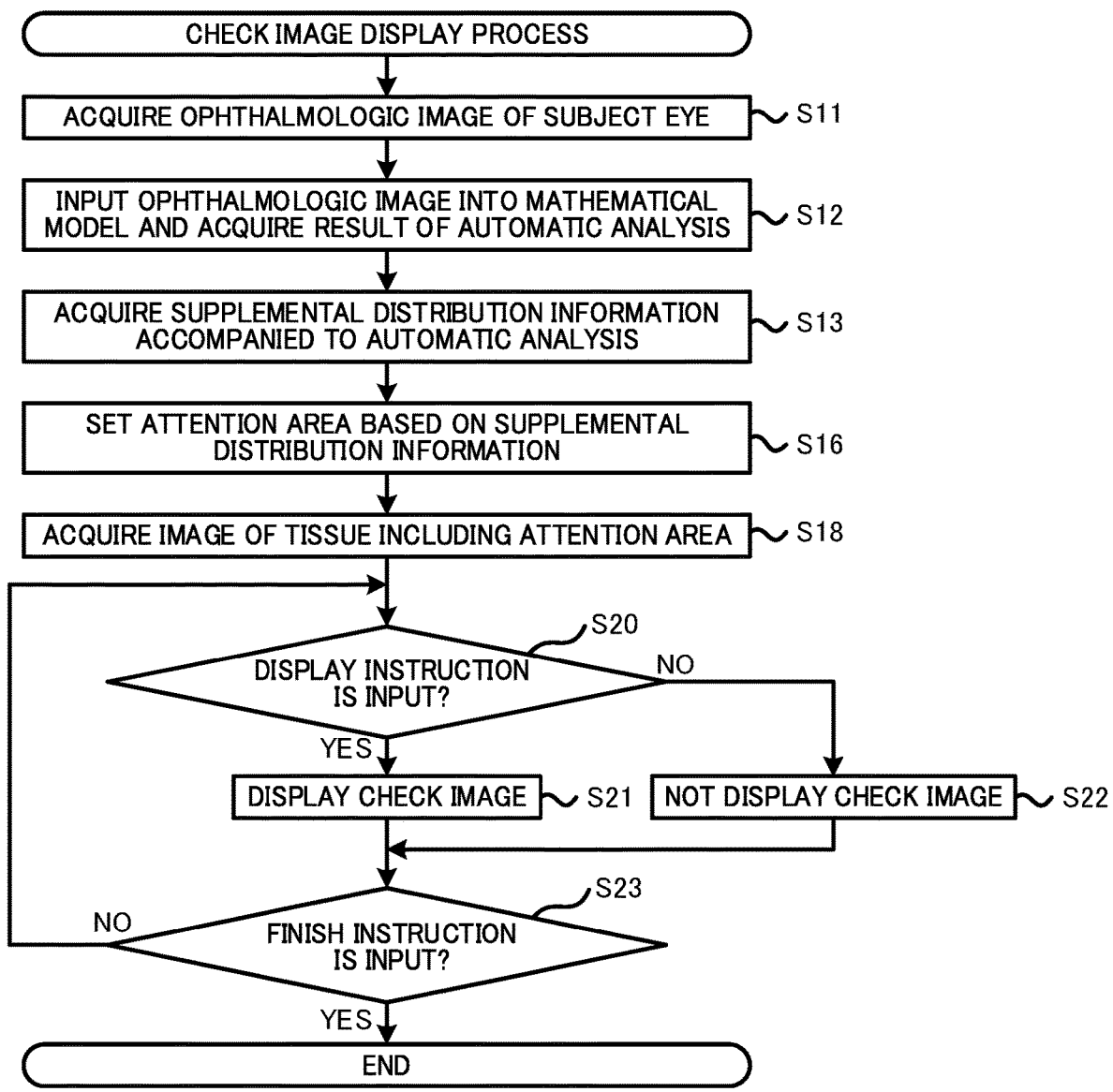
FIG. 7 is a flowchart illustrating a check image display process executed by the ophthalmologic image processing device 21.
Figure 10:
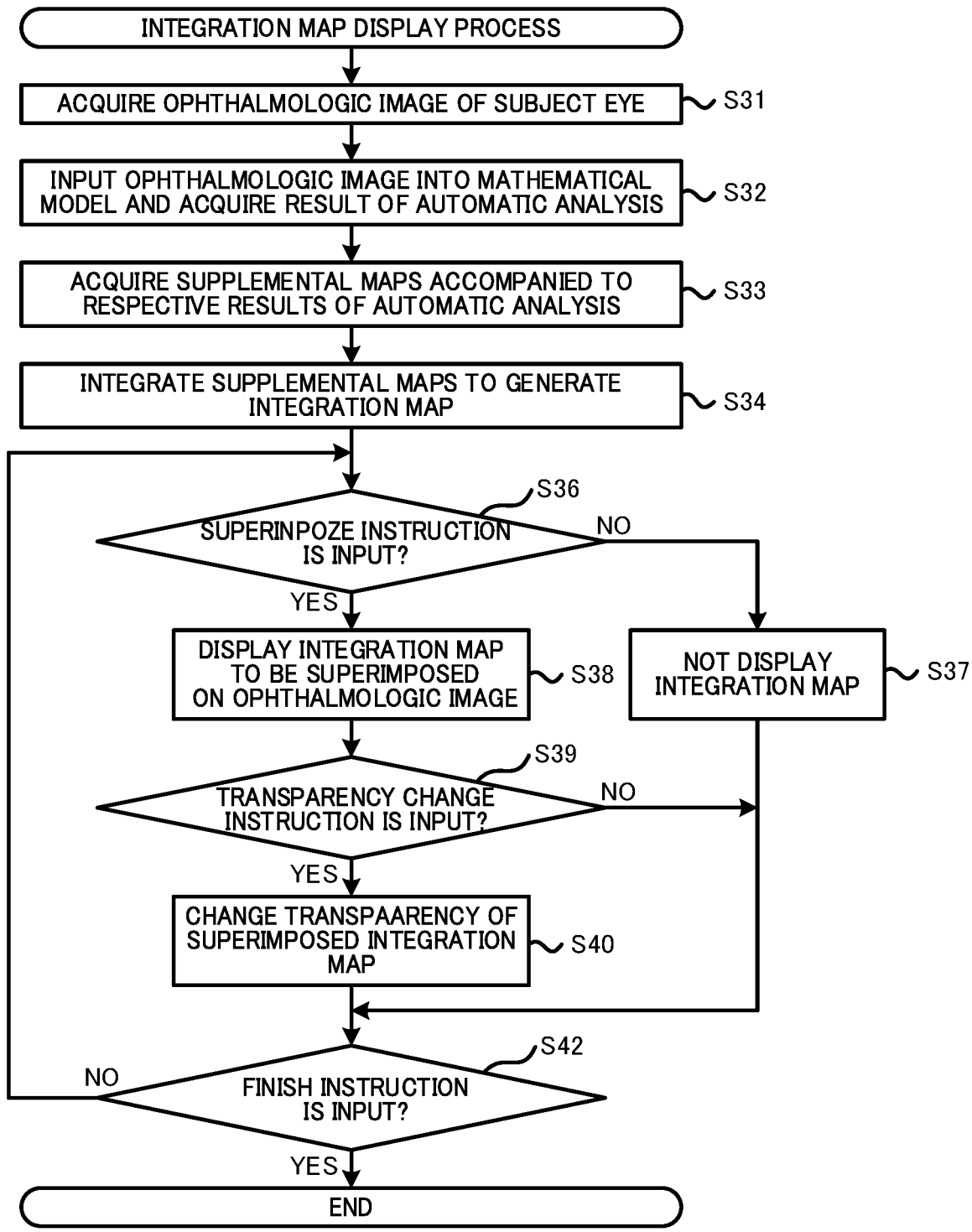
FIG. 10 is a flowchart illustrating an integration map display process executed by the ophthalmologic image processing device 21.

The process that acquires the ophthalmologic image in S11 shown in FIGS. 7 and S31 shown in FIG. 10 is one example of "acquiring ophthalmologic image". The process that acquires the result of the automatic analysis in S12 shown in FIGS. 7 and S32 shown in FIG. 10 is one example of "inputting the ophthalmologic image and acquiring a result of an analysis". The process that acquires the supplemental distribution information (supplemental map) in S13 shown in FIGS. 7 and S33 shown in FIG. 10 is one example of "acquiring information of a distribution" and "acquiring a supplemental map". The process that sets the attention area in S16 shown in FIG. 7 is one example of "setting the image area as an attention area". The process that displays the check image in S21 shown in FIG. 7 is one example of "acquiring an image and displaying the image". The process that generates and displays the integration map in S34 and S38 shown in FIG. 10 is one example of "acquiring an integration map displaying the integration map".

The apparatus and methods described above with reference to the various embodiments are merely examples. It goes without saying that they are not confined to the depicted embodiments. While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying principles.

What we claim is:

1. An ophthalmologic image processing device that processes an ophthalmologic image of a tissue of a subject eye, the ophthalmologic image processing device comprising a processor, wherein the processor:
acquires the ophthalmologic image photographed by an ophthalmologic image photographing device;
inputs the ophthalmologic image into a mathematical model trained by a machine learning algorithm and acquires a result of an analysis relating to at least one of a specific disease and a specific structure of a subject eye;
acquires information of a distribution of weight generated by the mathematical model, as supplemental distribution information, for which an image area of the ophthalmologic image input into the mathematical model is set as a variable, the supplemental distribution information including at least one from among (i) information indicating a distribution of a degree of influence that affects the result of the analysis relating to at least one of the specific disease and the specific structure output by the mathematical model, and (ii) information indicating a distribution of a degree of certainty of the analysis relating to at least one of the specific disease and the specific structure by the mathematical model;
sets a part of the image area of the ophthalmologic image, as an attention area, based on the supplemental distribution information;
acquires an image of a tissue including the attention area among a tissue of the subject eye with the ophthalmologic image photographing device that photographs the ophthalmologic image input to the mathematical model; and
displays the image of the tissue including the attention area on a display unit.

2. The ophthalmologic image processing device according to claim 1, wherein the processor sets an area of which the degree of certainty of the analysis relating to a specific disease or a specific structure is equal to or smaller than a threshold, within the image area of the ophthalmologic image, as the attention area.

3. The ophthalmologic image processing device according to claim 1, wherein the processor sets an area including a position of which the weight shown by the supplemental distribution is the largest or an area including a position of which the weight is equal to or larger than a threshold, within the image area of the ophthalmologic image, as the attention area.

4. The ophthalmologic image processing device according to claim 1, wherein the processor acquires a tomographic image of a part passing the attention area, among a tissue of the subject eye and displays the tomographic image on the display unit.

5. The ophthalmologic image processing device according to claim 1, wherein the processor extracts the image including the attention area from the ophthalmologic image for which a tissue of the subject eye is photographed and displays the extracted image area on the display unit.

6. The ophthalmologic image processing device according to claim 1, wherein the processor switches whether the image of a tissue including the attention area is displayed or is not displayed on the display unit, in accordance with an instruction input by a user.

7. An ophthalmologic image processing device that processes an ophthalmologic image of a tissue of a subject eye, the ophthalmologic image processing device comprising a processor, wherein the processor:
acquires the ophthalmologic image photographed by an ophthalmologic image photographing device;
inputs the ophthalmologic image into a mathematical model trained by a machine learning algorithm and acquires multiple results of analyses relating to different diseases or structures of a subject eye, the multiple results of analyses being obtained based on ophthalmologic images photographed by the ophthalmic image photographing device that photographs the ophthalmologic image input to the mathematical model;

acquires a supplemental map, for each of the results of the analyses, that indicates a distribution of weight relating to the analysis by the mathematical model, for which an image area of the ophthalmologic image input into the mathematical model is set as a variable, the supplemental map indicating at least one from among (i) a distribution of a degree of influence that affects the result of the analysis relating to at least one of the specific disease and the specific structure output by the mathematical model, and (ii) a distribution of a degree of certainty of the analysis relating to at least one of the specific disease and the specific structure by the mathematical model;

generates an integration map in which the supplemental maps are integrated within an identical area; and displays the integration map on a display unit.

8. The ophthalmologic image processing device according to claim 7, wherein the processor changes a display mode of each of the supplemental maps and integrates the supplemental maps to generate the integration map.

9. The ophthalmologic image processing device according to claim 7, wherein the processor displays the integration map to be superimposed on the ophthalmologic image of the subject eye.

10. The ophthalmologic image processing device according to claim 9, wherein the processor executes at least one of switching whether the integration map is displayed to be superimposed on the ophthalmologic image of the subject eye or is not displayed and changing a transparency of the integration map to be superimposed on the ophthalmologic image, in accordance with an instruction input by a user.

11. A non-transitory computer-readable storage medium storing computer-readable instructions that, when executed by a processor of an ophthalmologic image processing device, causes the ophthalmologic image processing device to perform processes comprising:

acquiring an ophthalmologic image photographed by an ophthalmologic image photographing device;

inputting the ophthalmologic image into a mathematical model trained by a machine learning algorithm and acquiring a result of an analysis relating to at least one of a specific disease and a specific structure of a subject eye;

acquiring information of a distribution of weight generated by the mathematical model, as supplemental distribution information, for which an image area of the ophthalmologic image input into the mathematical model is set as a variable, the supplemental distribution information including at least one from among (i) information indicating a distribution of a degree of influence that affects the result of the analysis relating to at least one of the specific disease and the specific structure output by the mathematical model, and (ii) information indicating a distribution of a degree of certainty of the analysis relating to at least one of the specific disease and the specific structure by the mathematical model;

setting a part of the image area of the ophthalmologic image, as an attention area, based on the supplemental distribution information;

acquiring an image of a tissue including the attention area among a tissue of the subject eye with the ophthalmologic image photographing device that photographs the ophthalmologic image input to the mathematical model; and displaying the image of the tissue including the attention area on a display unit.

* * * * *